(12) United States Patent
Zhang et al.

(10) Patent No.: US 8,729,303 B2
(45) Date of Patent: May 20, 2014

(54) 2,2',6,6'-TETRASUBSTITUTED AMINOPHOSPHINE LIGAND AND ITS SYNTHESIS METHOD

(75) Inventors: Wanbin Zhang, Shanghai (CN); Fang Xie, Shanghai (CN); Fang Fang, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 918 days.

(21) Appl. No.: 12/377,000

(22) PCT Filed: Aug. 10, 2007

(86) PCT No.: PCT/CN2007/002407
§ 371 (c)(1),
(2), (4) Date: Jun. 2, 2009

(87) PCT Pub. No.: WO2008/019598
PCT Pub. Date: Feb. 21, 2008

(65) Prior Publication Data
US 2010/0217040 A1    Aug. 26, 2010

(30) Foreign Application Priority Data
Aug. 10, 2006   (CN) .......................... 2006 1 0029881

(51) Int. Cl.
*C07F 9/02*        (2006.01)
(52) U.S. Cl.
USPC .......................................... 564/12
(58) Field of Classification Search
USPC .......................................... 564/12
See application file for complete search history.

(56) References Cited

U.S. PATENT DOCUMENTS

| | | |
|---|---|---|
| 5,919,981 A | 7/1999 | Chan et al. |
| 2002/0128501 A1 | 9/2002 | Zhang |
| 2010/0217040 A1 | 8/2010 | Zhang et al. |

FOREIGN PATENT DOCUMENTS

| | | |
|---|---|---|
| CN | 1911940 A | 2/2007 |
| JP | 2004-513950 A | 5/2004 |

OTHER PUBLICATIONS

International Search Report of PCT/CN2007/002407, Mailing Date of Nov. 1, 2007.
Japanese Office Action dated Nov. 6, 2012, issued in corresponding Japanese Patent Application No. 2009-523140, (4 pages). With English Translation.

*Primary Examiner* — Fereydoun G Sajjadi
*Assistant Examiner* — Amy C Bonaparte
(74) *Attorney, Agent, or Firm* — Westerman, Hattori, Daniels & Adrian, LLP

(57) ABSTRACT

The present invention relates to a 2,2',6,6'-tetrasubstituted aminophosphine ligand and its synthesis method. The structure of the ligand is shown as below. Its synthesis method comprises: Step (1) coupling 2,6-dinitrochlorobenzene as the starting material to obtain 2,2',6,6'-tetranitrobiphenyl; Step (2): hydrogenating the 2,2',6,6'-tetranitrobiphenyl with Pd/C to obtain 2,2',6,6'-tetraminobiphenyl; Step (3): reacting the 2,2',6,6'-tetraminobiphenyl with a phosphine halide to obtain the 2,2',6,6'-tetrasubstituted aminophosphine ligand. The ligand of the present invention is an achiral compound, and its preparation method is simple. The ligand can be converted to a chiral bimetallic catalyst with single configuration eventually through introduction of external chirality. Moreover, the ligand can be used in various asymmetric reaction catalyzed by metals with high reactivity and stereoselectivity.

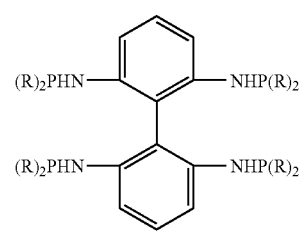

(1)

7 Claims, No Drawings

2,2',6,6'-TETRASUBSTITUTED AMINOPHOSPHINE LIGAND AND ITS SYNTHESIS METHOD

TECHNICAL FIELD

The present invention relates to an achiral ligand and its synthesis method, more specifically, to a 2,2',6,6'-tetrasubstituted aminophosphine ligand used in asymmetric catalytic reaction and its synthesis method.

BACKGROUND

Asymmetric catalysis is a good way to obtain chiral drugs of single enantiomer. It is capable of generating large amount of chiral compounds using small amount of catalysts, eliminating or even avoiding the production of ineffective compounds, which is not only environmentally beneficial, but also capable of achieving good atomic economy and avoiding complicated racemic resolution.

The design and synthesis of highly selective and catalytic chiral catalysts is of vital importance for the asymmetric catalysis. In an asymmetric reaction catalyzed by a transition metal, the chiral ligand coordinating with the metal is essential for the reactivity and enantioselectivity.

Since appearance of axial chiral ligand BINAP, the ligands having biphenyl or binaphthyl backbone have drawn much attention. Mainly due to the fact that the biphenyl or binaphthyl backbone with structural flexibility could spin freely along the axis, the catalytic systems derived from it have achieved rather good results in this art.

On the other hand, most asymmetric catalytic reaction systems have only one catalytic center which is activated through coordinating with the substrate and reagents, forming a thermodynamically stable transition state under the influence of chiral environment of the ligand, and achieving asymmetric induction eventually. Recently, much attention has been drawn to bimetallic ligands. The bimetallic ligand, as a new backbone of organometallics, may function through the coordination of two metals so as to afford excellent chemical selectivity and enantioselectivity for many reactions. Therefore, the development of bimetallic ligands having axial chirality has become a major research focus in both academic and industrial field.

Through a literature research in the prior art, no subject matter the same as or similar to that of the present invention is found up to now.

SUMMARY OF THE INVENTION

The object of the present invention is to provide a 2,2',6,6'-tetrasubstituted aminophosphine ligand and its synthesis method. The ligand may be used in various asymmetric reactions catalyzed by metals with high reactivity and stereoselectivity. This kind of ligand differs from the other bimetallic ligands in that this ligand is an achiral compound itself, and is readily to be prepared. Moreover, it may eventually generate a chiral bimetallic catalyst with a single configuration through introduction of external chirality.

The present invention is preformed through the following technical solution. The 2,2',6,6'-tetrasubstituted aminophosphine ligand of the present invention has the following formula (1) as shown below.

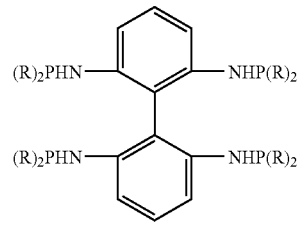

(1)

In formula (1) shown above, R represents a linear, branched or cyclic alkyl, aryl, or aralkyl group. The linear, branched or cyclic alkyl group described above, having preferably 1-18 carbons, may be exemplified as, specifically, methyl, ethyl, n-propyl, isobutyl, t-butyl, n-hexyl, isohexyl, n-heptyl, n-octyl, isooctyl, n-dodecyl, isododecyl, n-octadecyl, isooctadecyl, cyclopentyl, cyclohexyl, adamantyl and the like. In addition, the aryl group may be exemplified as phenyl, tolyl, xylyl, naphthyl and the like, and the aralkyl group may be exemplified as benzyl, phenethyl and the like. Wherein, the R in the formula is preferably a phenyl group.

The present invention also provides a method for synthesizing the 2,2',6,6'-tetrasubstituted aminophosphine ligand described above. The synthesis method of the present invention is characterized by reacting 2,2',6,6'-tetraminobiphenyl with a phosphine halide as shown by the formula of $(R)_2PX$ (wherein, R is defined as above, and X is a halogen atom), to produce the 2,2',6,6'-tetrasubstituted aminophosphine ligand.

The R in the formula of the phosphine halide describe above is equivalent to the R group in the formula of the 2,2',6,6'-tetrasubstituted aminophosphine ligand as shown by the formula (1) above. Further, the X in the formula of the phosphine halide described above represents a halogen atom, such as, chlorine, bromine, iodine and the like, wherein the chlorine atom is preferred.

The method for synthesizing the 2,2',6,6'-tetrasubstituted aminophosphine ligand of the present invention preferably comprises the following steps 1-3:

Step 1: coupling 2,6-dinitrochlorobenzene as the starting material, to obtain the 2,2',6,6'-tetranitrobiphenyl;

Step 2: hydrogenating the 2,2',6,6'-tetranitrobiphenyl with Pd/C, to obtain a 2,2',6,6'-tetraminobiphenyl;

Step 3: reacting the 2,2',6,6'-tetraminobiphenyl with a phosphine halide as shown by the formula of $(R)_2PX$ (wherein, R is defined as above, and X is a halogen atom), to produce the 2,2',6,6'-tetrasubstituted aminophosphine ligand.

The reaction scheme of the method of the present invention is shown as below:

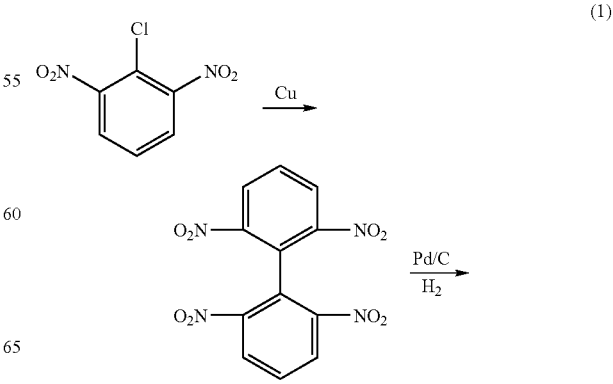

(1)

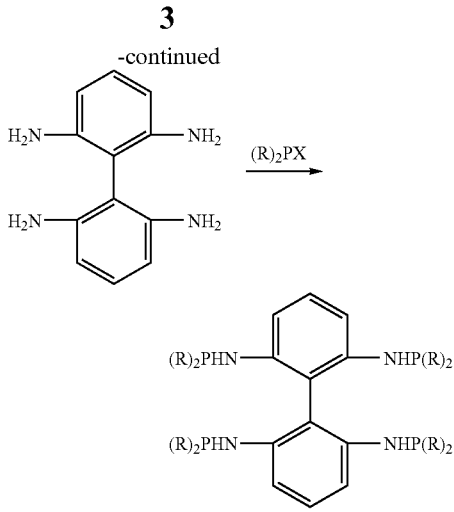

The reaction of Step 1 is specifically performed as follows. One equivalence of 2,6-dinitrochlorobenzene is mixed with 2-4 equivalences, and preferably 3 equivalences, of copper powder through solid phase reaction process. The resulting mixture is vigorously stirred to react at the temperature of 150-250° C., and preferably at the temperature of 180° C. The mixture is washed with, for example, ethyl acetate, and then filtered to remove the precipitate. The filtrate is concentrated, and is recrystallized from, for example, a mixed solution of ethyl acetate and petroleum ether.

The reaction of Step 2 is specifically performed as follows. The Pd/C of 5-15%, and preferably 10%, relative to the mass of the substrate, is added as the catalyst to the 2,2',6,6'-tetranitrobiphenyl. The hydrogen gas of 5-20 atm, and preferably 10 atm, is added to the autoclave. Upon completion of the reaction, the solid is filtered off, and the filtrate is concentrated, to afford the 2,2',6,6'-tetraminobiphenyl.

The reaction of Step 3 is specifically performed as follows. The 3-7 equivalences, and preferably 5 equivalences, of phosphine halide as described above is added into 1 equivalence of 2,2',6,6'-tetraminobiphenyl using, for example, dichloromethane or tetrahydrofuran as the solvent, and triethylamine or butyl lithium as the base. The mixture is reacted to afford the 2,2',6,6'-tetrasubstituted aminophosphine ligand.

The 2,2',6,6'-tetrasubstituted aminophosphine ligand of the present invention has four coordination centers. This kind of ligand may be applied to various asymmetric reactions catalyzed by metals, such as, asymmetric hydrogenation of ketone, asymmetric cyclopropanation reaction, intramolecular Wacker-Type cyclization reaction, asymmetric oxidation reaction of alkene and intramolecular [2+1] cycloaddition reaction and the like, with high reactivity and stereoselectivity, which shows great potential in future applications.

EMBODIMENT OF THE INVENTION

Examples are provided below in reference of the technical content of the present invention.

Example 1

1. Preparation of 2,2',6,6'-tetranitrobiphenyl

Pre-treatment of copper powder: The copper powder (5.0 g, 78 mmol) was weighted and added into to a 20 mL of 2% iodine/acetone solution. The mixture was stirred for 10 minutes, and filtered in vacuum. The resultant was added into 20 mL of mixed solution of acetone:hydrochloric acid=1:1. The resultant mixture was stirred for 10 minutes, filtered, and dried in vacuum. The 2,6-dinitrochlorobenzene (3.04 g, 15 mmol) and copper powder (2.88 g, 45 mmol) were added into a 250 mL round flask, and were mixed homogeneously. Under the protection of nitrogen gas, the mixture was heated at 180° C. under stirring in an oil bath for two hours. Upon completion of the reaction, the solid in the flask was grounded, and dissolved in 20 mL of ethyl acetate. The solid was filtered off, and the filtration was collected and rotary evaporated. The residue was recrystallized from a mixed solution of ethyl acetate: petroleum ether=10:1, to precipitate a pale yellow needle-like crystal. The crystal was filtered in vacuum, to afford the product in a yield of 63.9%.

$^1$H NMR (400 MHz, CDCl$_3$): 7.89 (t, 2H, J=8.0 Hz, ArH), 8.51 (d, 4H, J=8.0 Hz, ArH).

Melting point: 217° C.-218° C.

2. Preparation of 2,2',6,6'-tetraminobiphenyl

Under the protection of nitrogen gas, the 2,2',6,6'-tetranitrobiphenyl (1.00 g, 3 mmol) and 100 mg 10% Pd/C were added into a 100 mL hydrogenation flask. Subsequently, 20 mL of methanol is added, and the resultant mixture was bubbled with nitrogen gas. The hydrogenation flask was placed in an autoclave, and was added 10 atm of hydrogen gas. After 6 hours, the reaction is completed. The resultant was filtered to remove Pd/C, and was rotary evaporated to remove the methanol. The residue was extracted with ethyl acetate and water, dried over anhydrous sodium sulfate, filtered, and votary evaporated, to afford the product in a yield of 88%.

$^1$H NMR (400 MHz, CDCl$_3$): 6.99 (t, 2H, J=8.0 Hz, ArH), 6.25 (d, 4H, J=8.0 Hz, ArH), 3.3-3.8 (brs, 8H, NH)

Melting point: 204° C.

3. Preparation of 2,2'6,6'-tetra(diphenylphosphino) aminodiphenyl

The 2,2',6,6'-tetraminobiphenyl (107.90 mg, 0.5 mmol) was dissolved in 10 mL of dichloromethane. The resultant solution was added triethylamine (0.56 mL, 4 mmol) and diphenylphosphinochloride (0.45 mL, 2.5 mmol) consecutively by dropping. The mixture was refluxed at stirring at 50° C. for 24 hours. The resultant solution was cooled, concentrated, and added with 5 mL of anhydrous diethyl ether. The precipitate was filtered, and was washed with 5 mL of anhydrous diethyl ether. The resultant was purified through column chromatography using ethyl acetate/petroleum=1:5 as the eluent, to afford the target product in a yield of 76%.

$^1$H NMR (400 MHz, CDCl$_3$): 7.09-7.21 (m, 44H, ArH), 6.87 (d, 2H, J=2.8 Hz, ArH), 6.86 (d, 2H, J=2.8 Hz, ArH), 4.53 (d, 4H, J=5.2 Hz, NH).

Example 2

1. Preparation of 2,2',6,6'-tetranitrobiphenyl (the same as Example 1)

2. Preparation of 2,2',6,6'-tetraminobiphenyl (the same as Example 1)

3. Preparation of 2,2'6,6'-tetra(diphenylphosphino) aminodiphenyl

The 2,2',6,6'-tetraminobiphenyl (107.90 mg, 0.5 mmol) was dissolved in 10 mL of tetrahydrofuran. The reaction was cooled to −30° C., into which a solution of n-butyl lithium (2.57 M, 0.78 mL) in n-hexane is added. After stirring at this temperature for two hours, the diphenylphosphinochloride (0.45 mL, 2.5 mmol) was added by dropping. The temperature was increased to 25° C., and the reaction was stirred for a further five hours. The precipitate was filtered off, and the tetrahydrofuran was evaporated. The residue was purified through column chromatography using ethyl acetate/petroleum=1:5 as the eluent, to afford the target product in a yield of 83%.

The invention claimed is:

1. A 2,2',6,6'-tetrasubstituted aminophosphine ligand, wherein, said 2,2',6,6'-tetrasubstituted aminophosphine ligand has the following formula (1):

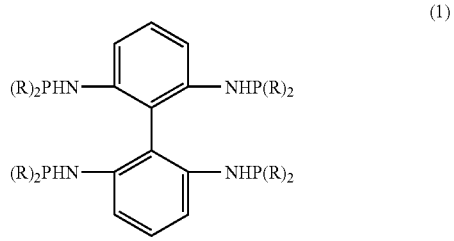

(1)

wherein, R represents a linear, branched or cyclic alkyl, aryl, or aralkyl group.

2. A 2,2',6,6'-tetrasubstituted aminophosphine ligand as defined in claim 1, wherein,
in the formula (1), R is a phenyl group.

3. A method for synthesizing the 2,2',6,6'-tetrasubstituted aminophosphine ligand as defined in claim 1, comprising
reacting a 2,2',6,6'-tetraminobiphenyl with a phosphine halide having the formula of $(R)_2PX$, wherein, R is defined as above, and X is a halogen atom.

4. A method for synthesizing the 2,2',6,6'-tetrasubstituted aminophosphine ligand as defined in claim 1, comprising:
Step 1: coupling 2,6-dinitrochlorobenzene as the starting material, to obtain a 2,2',6,6'-tetranitrobiphenyl;
Step 2: hydrogenating the 2,2',6,6'-tetranitrobiphenyl with palladium on carbon (Pd/C), to obtain a 2,2',6,6'-tetraminobiphenyl;
Step 3: reacting the 2,2',6,6'-tetraminobiphenyl with a phosphine halide having the formula of $(R)_2PX$, wherein, R is defined as above, and X is a halogen atom.

5. The method for synthesizing the 2,2',6,6'-tetrasubstituted aminophosphine ligand as defined in claim 4, wherein,
the Step 1 is performed by mixing 2,6-dinitrochlorobenzene with copper powder through a solid phase reaction process.

6. The method for synthesizing the 2,2',6,6'-tetrasubstituted aminophosphine ligand as defined in claim 4, wherein,
Step 2 is performed by adding Pd/C as the catalyst to the 2,2',6,6'-tetranitrobiphenyl, and reacting in the presence of hydrogen.

7. The method for synthesizing the 2,2',6,6'-tetrasubstituted aminophosphine ligand as defined in claim 4, wherein,
Step 3 is performed by adding phosphine halide into the 2,2',6,6'-tetraminobiphenyl, and reacting in an alkaline condition.

* * * * *